(12) United States Patent
Bureau et al.

(10) Patent No.: US 10,292,641 B2
(45) Date of Patent: May 21, 2019

(54) INTEGRATED INJECTION SYSTEM AND COMMUNICATION DEVICE

(71) Applicant: Becton Dickinson France S.A.S., Le Pont de Claix (FR)

(72) Inventors: Christophe Bureau, Saint-Martin d'Uriage (FR); Roderick Hausser, Kinnelon, NJ (US); Herve Monchoix, St. Ismier (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 230 days.

(21) Appl. No.: 14/413,536

(22) PCT Filed: Jul. 10, 2013

(86) PCT No.: PCT/US2013/049881
§ 371 (c)(1),
(2) Date: Jan. 8, 2015

(87) PCT Pub. No.: WO2014/011740
PCT Pub. Date: Jan. 16, 2014

(65) Prior Publication Data
US 2015/0201880 A1    Jul. 23, 2015

Related U.S. Application Data

(60) Provisional application No. 61/669,846, filed on Jul. 10, 2012.

(51) Int. Cl.
*A61M 5/172* (2006.01)
*A61B 5/00* (2006.01)
(Continued)

(52) U.S. Cl.
CPC .......... *A61B 5/4833* (2013.01); *A61B 5/0002* (2013.01); *A61B 5/02055* (2013.01);
(Continued)

(58) Field of Classification Search
None
See application file for complete search history.

(56) References Cited

U.S. PATENT DOCUMENTS 6,425,878 B1 * 7/2002 Shekalim ................. A61B 5/01
600/384
2002/0040208 A1 * 4/2002 Flaherty ............ A61M 5/14248
604/288.01
(Continued)

FOREIGN PATENT DOCUMENTS

CN    101143234 A    3/2008
JP    60501790 A    10/1985
(Continued)

*Primary Examiner* — Erica S Lee
(74) *Attorney, Agent, or Firm* — The Webb Law Firm

(57) ABSTRACT

An integrated system for injection including an injection device (10) in electronic connection with a communication device (A) is provided. The external communication device may be a handheld electronic device such as a Smartphone or a dedicated reader such as a reader capable of reading information contained on an RFID tag. The injection device includes a needle (12) and a drug delivery portion (28) enclosed within an external housing. Optionally, a plurality of sensors (16) is affixed to the surface of the needle to collect data about the injection and physical characteristics of the patient. The data may be recorded on a data capture module (36). The electronic chip may be a readable and writable electronic chip such as a nonvolatile memory chip. The injection device may further include a data transmitter (42) for sending information obtained from the data capture module to the external communications device.

25 Claims, 12 Drawing Sheets

(51) Int. Cl.
*A61M 37/00* (2006.01)
*A61B 5/0205* (2006.01)
*A61M 5/158* (2006.01)
*A61M 5/20* (2006.01)
*A61M 5/142* (2006.01)
*A61B 5/01* (2006.01)
*A61B 5/0215* (2006.01)
*A61B 5/024* (2006.01)
*A61B 5/021* (2006.01)

(52) U.S. Cl.
CPC .......... *A61B 5/4839* (2013.01); *A61B 5/4866* (2013.01); *A61B 5/4872* (2013.01); *A61B 5/6848* (2013.01); *A61B 5/6898* (2013.01); *A61B 5/742* (2013.01); *A61B 5/7475* (2013.01); *A61M 5/158* (2013.01); *A61M 5/1723* (2013.01); *A61M 5/20* (2013.01); *A61M 37/0015* (2013.01); *A61B 5/002* (2013.01); *A61B 5/01* (2013.01); *A61B 5/021* (2013.01); *A61B 5/024* (2013.01); *A61B 5/0215* (2013.01); *A61B 5/02438* (2013.01); *A61B 2560/0214* (2013.01); *A61B 2560/0462* (2013.01); *A61B 2562/08* (2013.01); *A61M 5/142* (2013.01); *A61M 2005/1588* (2013.01); *A61M 2005/1726* (2013.01); *A61M 2037/0023* (2013.01); *A61M 2037/0061* (2013.01); *A61M 2205/0294* (2013.01); *A61M 2205/3576* (2013.01); *A61M 2205/502* (2013.01); *A61M 2230/00* (2013.01)

(56) References Cited

U.S. PATENT DOCUMENTS

| | | |
|---|---|---|
| 2003/0153900 A1 | 8/2003 | Aceti et al. |
| 2004/0024348 A1* | 2/2004 | Redding, Jr. ........ A61K 9/0009 604/22 |
| 2004/0122297 A1 | 6/2004 | Stahmann et al. |
| 2005/0192557 A1* | 9/2005 | Brauker ................ A61B 5/0002 604/503 |
| 2009/0088662 A1* | 4/2009 | Larsen ............. A61M 5/16836 600/547 |
| 2011/0288499 A1 | 11/2011 | Forsell |

FOREIGN PATENT DOCUMENTS

| | | |
|---|---|---|
| JP | 2004524869 A | 8/2004 |
| JP | 2011500290 A | 1/2011 |
| JP | 2011120921 A | 6/2011 |
| JP | 2011517581 A | 6/2011 |
| WO | 2007112034 A2 | 10/2007 |
| WO | 2010098927 A1 | 9/2010 |

* cited by examiner

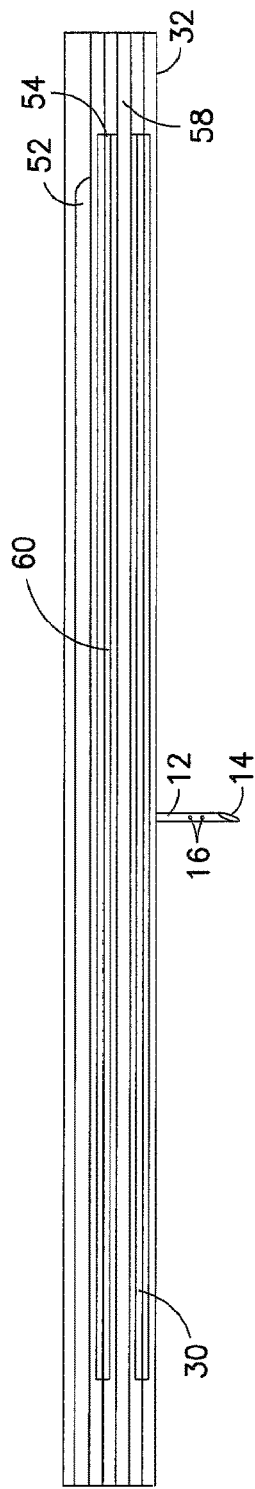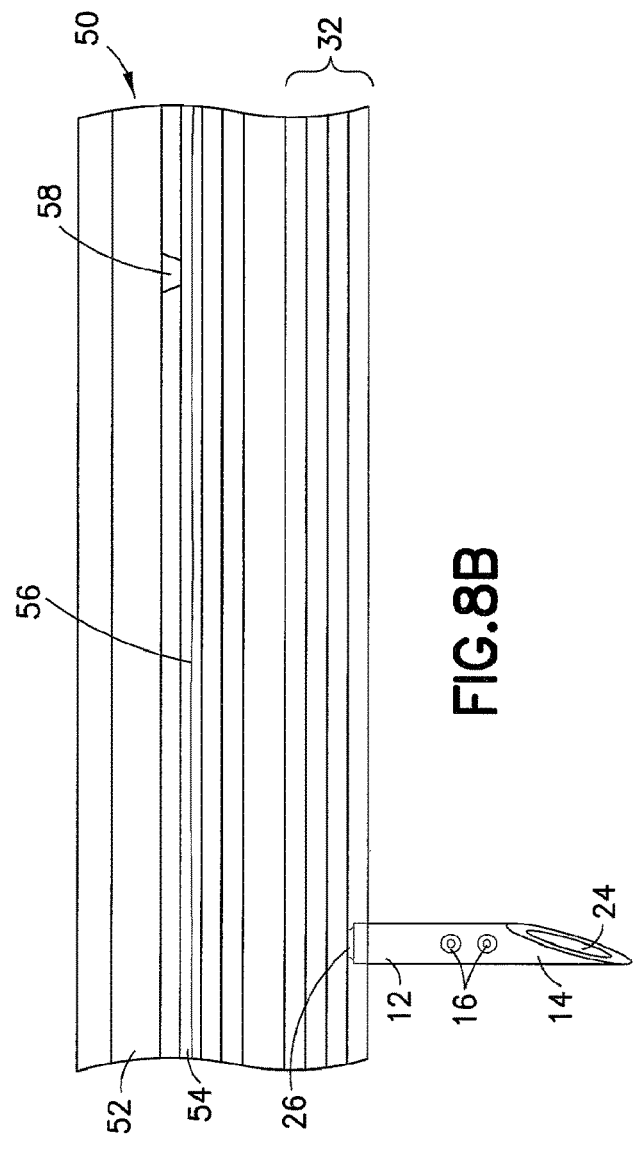
FIG.8A
FIG.8B

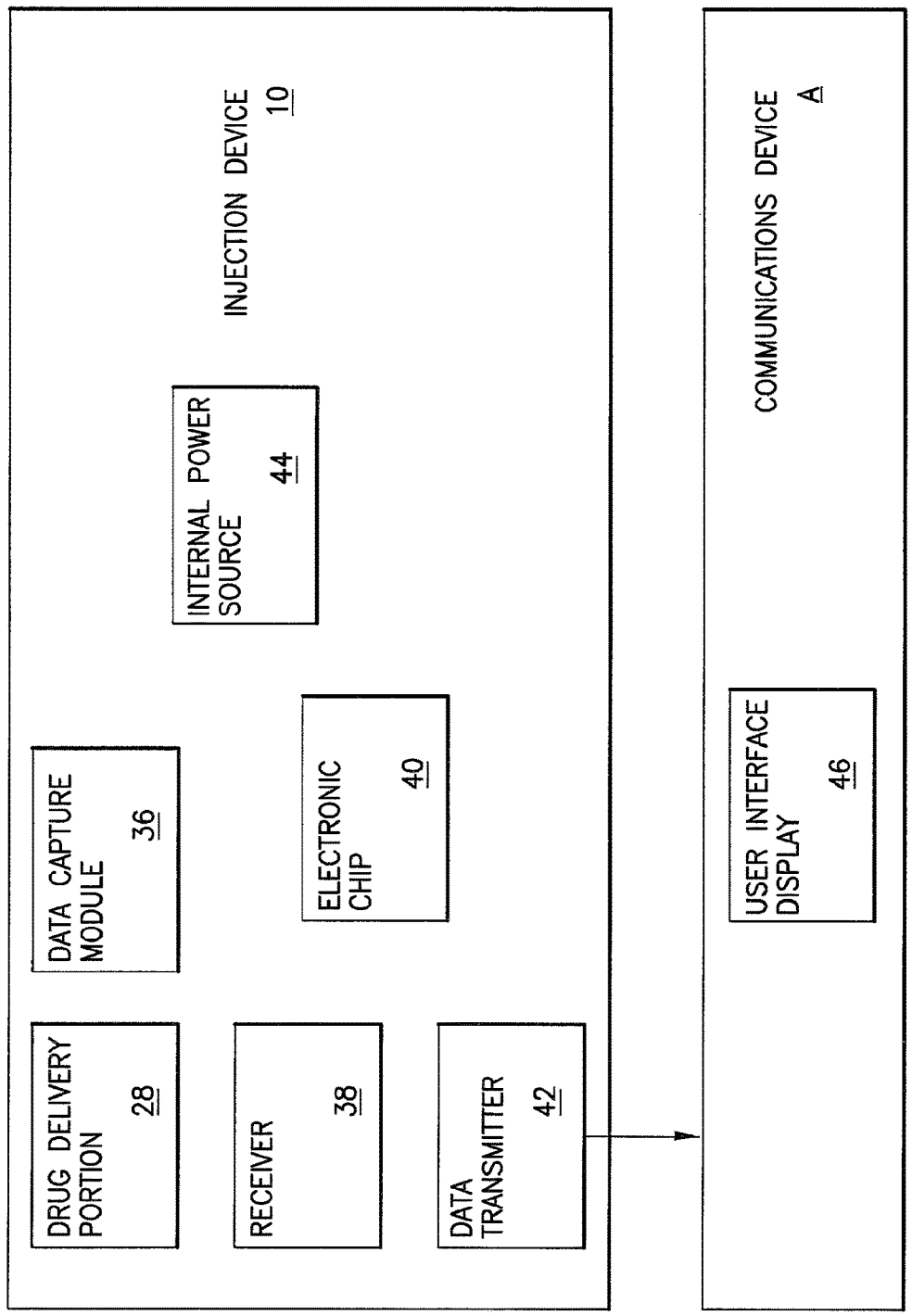

INTEGRATED INJECTION SYSTEM AND COMMUNICATION DEVICE

CROSS-REFERENCE TO RELATED APPLICATIONS

This application is the U.S. national phase of International Application No. PCT/US2013/049881 filed Jul. 10, 2013, and claims priority to U.S. Provisional Patent Application No. 61/669,846 filed Jul. 10, 2012, the disclosures of which are hereby incorporated in their entirety by reference.

BACKGROUND OF THE INVENTION

Field of the Invention

The present invention relates generally to an integrated injection system including an injection device that collects and transmits data regarding the injection event and physical characteristics of the patient to a receiver.

Description of Related Art

In the healthcare community, it is generally accepted that the cost-per-capita must decrease. Notably, as populations age and as countries have less money to spend on healthcare costs, the amount of money available for healthcare expenditures per person will necessarily decrease. Consequently, patients will perform greater numbers of treatments by themselves to eliminate the cost associated with visiting a healthcare professional for simple (e.g., non-diagnostic) procedures. This is already occurring for patients affected by diabetes, rheumatoid arthritis, or multiple sclerosis and could become the standard for other treatments including contraceptives, cosmetics, or vaccines in the future. Individuals who perform treatments on themselves have different needs and requirements than patients receiving treatment from a trained professional. Accordingly, the types of medication dispensing apparatuses attractive to un-trained individuals will be different than the types of apparatuses used by trained medical professionals.

Rapidly increasing health care costs require medical providers to reevaluate how medication is provided to patients and how the efficacy of prescribed medication is evaluated. For example, it is necessary to have better control over the supply of and demand for medications. It is also necessary to better manage chronic diseases, since chronic patients account for the largest portion of healthcare costs. Specifically, over-expenditure for chronic patients is common as a result of patients failing to follow prescribed treatments. In addition, there is a need to focus on prevention and early detection of potential health hazards.

Currently, patient adherence to prescribed treatments is generally based on information self-reported to the medical provider by the patient. The patient may keep a journal including information such as when the medication was taken and some diagnostic information such as, in the case of diabetes, glucose level. It is noted that, in each of these instances, the patient has significant responsibility for treatment and, in some cases, diagnosis. Not only must the patient take the prescribed amount of the medication at the correct time, but must also document that the medication was ingested or injected, perform tests (i.e., a blood test for insulin levels), record the results, and, in some instances, interpret the results to determine whether additional medication must be taken. As the number of activities that the patient must perform increases, the possibility for patient non-adherence to provided instructions also increases.

Alternatively, a patient may visit a medical facility at various intervals to have tests performed during the course of a medication treatment regime. Requiring additional visits to medical facilities for diagnostic procedures increases healthcare costs. In addition, patients often view testing and diagnostic costs as less important than treatment and, as a result, are less willing to incur such testing expenses. Therefore, patients will either forego the prescribed testing while still taking the medication or avoid treatment options altogether which require additional testing during the course of the treatment regime.

Therefore, there is a need for an injection device which is capable of extracting information from the patient to provide an indication of the patient's health during the treatment activity. The information should be quickly and automatically made available to a medical professional in order to trigger an ongoing diagnosis and to modify the treatment regime if necessary. The information about patient adherence to prescribed treatments and physical condition should be able to be correlated along with data from other patients to determine when patients are most likely to follow treatment instructions and to better understand reasons why patients fail to follow treatment instructions. The data may also be used to coach the patient on how to better follow the prescribed treatment and, if necessary, modify the treatment options so that patient adherence is further encouraged.

SUMMARY OF THE INVENTION

An embodiment of the present invention is directed to an integrated system for injection including an injection device in electronic connection with a communication device. The external communication device may be a handheld electronic device such as a Smartphone or a dedicated reader such as a reader capable of reading information contained on an RFID tag. The injection device includes a needle, drug delivery portion, and external housing. Optionally, a data capture module including a plurality of sensors is affixed to the surface of the needle. The injection device further comprises an electronic chip having the capability of storing information about the injection and about the physical condition of the patient. The electronic chip may be a readable and writable electronic chip such as a non-volatile memory chip, for example, an electrically erasable programmable read-only memory (EEPROM). Alternatively, the electronic chip may be a passively read RFID tag. The injection device may further include a data transmitter for sending information obtained from the data capture module to the external communications device.

In certain configurations, the data transmitter is a hard wired connection such as a USB or Firewire port. Alternatively, the data transmitter may be a wireless communications module including a wireless antenna.

In certain configurations, the injection device further includes a power source such as a battery. Alternatively, the injection device may be configured to receive power either directly or wirelessly from an external device such as a Smartphone.

The present invention further includes a miniaturized drug delivery portion which includes a reservoir containing a fluid to be delivered to a user, and a microneedle in fluid communication with the reservoir and extendable through at least a portion of the housing. In accordance with an embodiment of the present invention, the microneedle of the drug delivery portion is configured for intradermal injection. Optionally, the microneedle is configured to extend from the housing about 2 mm allowing for an injection to a depth of 2 mm. In another configuration, the microneedle is configured to extend from the housing about 1 mm allowing for an injection to a depth of 1 mm.

In another configuration of the drug delivery portion, the fluid containing reservoir contains a single dose of a therapeutic agent. Further, the drive mechanism expels fluid from the reservoir as a single continuous dose delivered at a standard clinical dose rate. Optionally, the clinical rate is about 10 seconds.

According to another embodiment of the present invention, the drug delivery component of the injection device further includes an activator for engaging the drive mechanism. Further, once engaged by the activator, the drive mechanism passively expels fluid from the reservoir. The activator may be located on the housing of the device. Alternatively, the activator is triggered by an activation activity performed by a user on an external device such as a smart phone or other remote deployment.

In another embodiment of the self-injection device, the device further includes an indicator which alerts a user when the fluid has been fully expelled from the reservoir completing the injection. Optionally, the indicator is an external indication appearing on an external device such as a smart phone or other remote deployment device.

In another configuration of the reservoir of the drug delivery portion of the device, the drug delivery portion further includes a pierceable septum located on a wall of the reservoir for accessing the reservoir when filling the reservoir. Optionally, the pierceable septum is self-sealing.

In accordance with another embodiment of the present invention, an intradermal injection device includes a non-traditional activation mechanism for initiating expulsion of a fluid from a housing, a mechanism for reducing the perception of pain in the recipient of the fluid expelled from the housing, and a feedback mechanism for externally providing information regarding the completion of the expulsion of fluid from the housing to the patient.

In one configuration, the feedback mechanism includes an end-of-dose indication. In another configuration, the feedback mechanism includes transmission of information regarding completion of treatment to a third party.

In accordance with an embodiment of the present invention, an integrated injection system includes an injection device comprising a drug delivery portion, a data transmitter, and a data capture module including at least one sensor. The data capture module is configured to sense information about a physical condition and/or a behavior of a patient during an injection event. The data transmitter is configured to be in electronic communication with a communication device that is external to the injection device, and the data transmitter is also configured to transmit at least a portion of the sensed information to the communication device.

The drug delivery portion may include a needle, and the at least one sensor may be located on a portion of the needle which is intended to be positioned inside the body of the patient during the injection event. The at least one sensor may be positioned within the body of the patient during the injection event.

In certain configurations, the injection device further includes an external housing enclosing the drug delivery portion and the data transmitter, wherein the drug delivery portion includes a reservoir containing a pharmaceutical agent to be delivered to the patient, and wherein the needle is in fluid communication with the reservoir and extendable through at least a portion of the external housing. The data transmitter may be configured to transmit a signal to the communication device when the pharmaceutical agent has been fully expelled from the reservoir. In certain configurations, the communication device is configured to provide an indication which alerts a user that the pharmaceutical agent has been expelled from the reservoir in response to the signal. The drug delivery portion may include an activator configured to engage a drive mechanism configured to expel a pharmaceutical agent from the injection device, and the activator may be configured to be triggered by an activation activity performed by a user on the communication device.

In other configurations, the sensor is configured to measure a physical characteristic of the patient. The physical characteristic may be metabolism, body temperature, heart rate, blood pressure, or body fat composition. The communication device may be configured to analyze at least a portion of the sensed information to determine adherence to a prescribed treatment routine. The communication device may also be configured to analyze the sensed information in correlation with data obtained from other sources to determine adherence to a prescribed treatment routine.

At least one of the injection device and the communication device may be configured to store the sensed information from a plurality of different injection events. The injection device may also include an electronic chip configured to store the sensed information. The electronic chip may be further configured to store information identifying at least one of a type of injection device, an injection time of the injection event, or an injection location of the injection event. The electronic chip may also be configured to store additional information pertaining to a manufacturing or a distribution process of the injection device.

The data transmitter may include a wireless transmitter such that the electronic communication with the communication device is performed wirelessly. Alternatively, the data transmitter may include a wired connection including a pin connector configured for insertion into a corresponding port of the communication device such that the electronic communication with the communication device is performed over the wired connection. Optionally, the injection device further includes an internal power source. Alternatively, the injection device is configured to receive power from the communication device.

In certain embodiments, the communication device is configured to transmit at least a portion of the sensed information to at least one external system. The communication device may include a user interface display configured to provide at least a portion of the sensed information to a user.

In other configurations, the injection system further includes a pharmaceutical agent within the drug delivery portion with the sensor being configured to detect whether or not the pharmaceutical agent was successfully injected into the body of the patient. In certain configurations, the injection system also includes a receiver device configured to be placed on an area of the body of the patient during the injection event. The injection device is configured to send an electrical signal with a predefined waveform through a needle into the body of the patient, and the receiver device is configured to identify and process the predefined waveform to determine if the pharmaceutical agent was injected into the body of the patient. Optionally, the communication device may be a smart phone.

In accordance with another embodiment of the present invention, an integrated injection device includes an injection device having a drug delivery portion, a data transmitter, and a data capture module including at least one sensor. The data capture module is configured to sense information about a physical condition and/or a behavior of a patient during an injection event. The data transmitter is configured to be in electronic communication with a communication device that is external to the injection device, and the data transmitter is also configured to transmit at least a portion of the sensed information to the communication device.

In accordance with another embodiment of the present invention, a method for monitoring an injection event includes delivering, by an injection device, a pharmaceutical agent to the body of a patient. The method also includes sensing, by at least one sensor of a data capture module of the injection device, information about a physical condition and/or a behavior of the patient during the injection event, and establishing, by a data transmitter of the injection device, an electronic communication with a communication device that is external to the injection device. The method further includes transmitting, by the data transmitter of the injection device, at least a portion of the sensed information to the communication device.

BRIEF DESCRIPTION OF THE DRAWINGS

For the purpose of facilitating understanding of the invention, the accompanying drawings and description illustrate preferred embodiments thereof, from which the invention, various embodiments of its structures, construction and method of operation, and many advantages may be understood and appreciated.

FIG. 8A is a side view of the drug delivery portion of the injection device in accordance with an embodiment of the present invention.

FIG. 8B is an enlarged partial side view of the drug delivery portion of FIG. 8A in accordance with an embodiment of the present invention.

FIG. 13 is a block diagram of a combined injection device and communications device in accordance with an embodiment of the present invention.

DESCRIPTION OF THE PREFERRED EMBODIMENTS

Figure 1A:
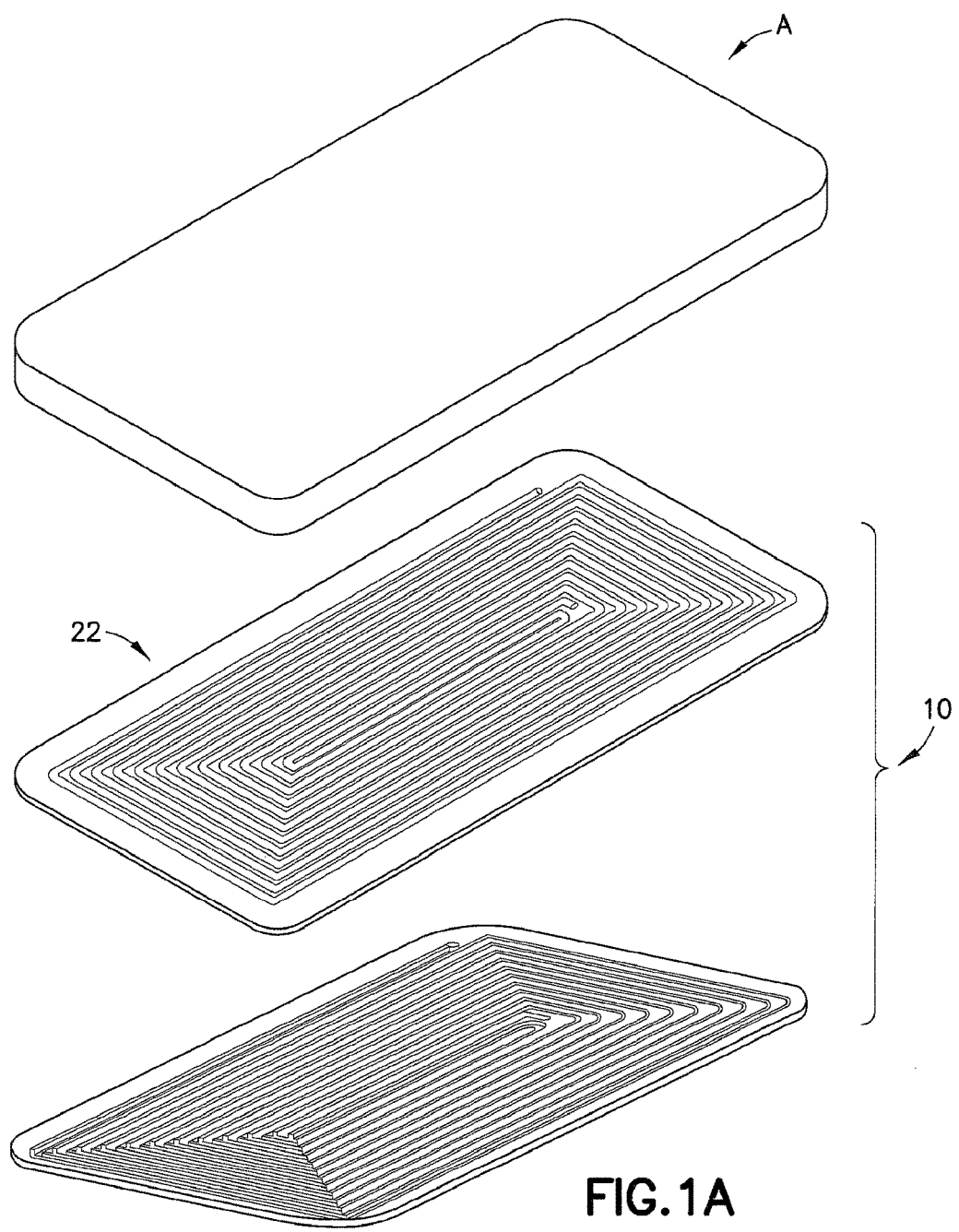
FIG. 1A is an exploded perspective view of a combined injection device and Smartphone in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to FIGS. 1A-5B and 13, the present invention is directed to an integrated injection system and communication device which includes an injection device 10. The injection device may include a drug delivery portion 28, a data capture module 36 including at least one sensor 16, a receiver 38, an electronic chip 40, a data transmitter 42 in communication with a communications device A and/or an internal power source 44. The communication device A may be a smartphone including a user interface display 46. The injection device 10 is capable of sensing and recording information about the physical condition and behavior of a patient during an injection event. Specifically, a needle 12 is inside the body of the patient and, consequently, ideally positioned to access tissue samples to obtain data concerning the patient's metabolism. In one non-limiting embodiment of the invention, sensors 16 are implanted on a distal end 14 of the needle 12 to measure metabolism and other physical characteristics. The sensors may be any type of commercially available sensors of appropriate size, which provide information useful for estimating metabolism, including, but not limited to, sensors that measure body temperature, heart rate, blood pressure, or body fat composition. Metabolism data can be used to draw general conclusions about the patient's behavior such as adherence to a prescribed treatment regime, physical activity, overall health, and physical well-being. For patients who have regularly scheduled injections, data can be collected on a consistent basis, thereby providing an indication of the change of physical parameters over time. The data can be captured, stored, and correlated with evidence obtained from other sources to draw even more conclusions about the patient's behavior and physical state. Inserting a needle 12 into a patient's body provides a convenient way to measure physical characteristics, such as metabolism, without requiring the patient to undergo additional medical testing procedures. Specifically, the injection device 10 may be used to collect data for patient's suffering from chronic conditions such as diabetes, rheumatoid arthritis, multiple sclerosis, or from more temporary conditions which, nevertheless, require a consistent administration of medication through injection.

In other configurations, the injection system of the present invention can be used to collect patient health data for a generally healthy patient who would not otherwise be available for medical testing. For example, a healthy individual who receives annual flu shots, may have no other interaction with medical personnel throughout the year. Therefore, the annual vaccination is the sole time when data could be collected which would not impose an additional requirement on the individual. Therefore, collecting data during the vaccination offers an attractive way to ensure that an individual is sufficiently monitored without imposing additional requirements that the individual may simply ignore or fail to perform.

The needle 12 of the present invention may be adapted for use with any known injection device 10 in which a needle enters a patient's skin tissue, including, but not limited to, stand-alone hypodermic needles, pen needles, autoinjectors, catheters, miniaturized self-injection devices, drug delivery patches, and others. The present invention focuses on taking advantage of the fact that the distal end 14 of the needle 12 is inserted into the patient for drug delivery as an opportunity to collect useful patient data to be used for diagnosis, recorded for comparison with later values, or correlated to draw conclusions about patient behavior.

In some embodiments, the system further includes a communications mechanism which is configured to make the measured data available remotely either by downloading data directly to a data management system all at once after the injection is completed, or by simultaneous transfer of data through a wired or wireless data transmission system. Data may be transferred to any number of stakeholders who have an interest in patient physical condition and adherence to treatment including, but not limited to, care-givers (both family members and responsible healthcare professionals), pharmacists, doctors, hospitals, clinics, accountable care organizations, pharmacy benefit managers, disease management companies, pharmaceutical companies, insurance companies, social service providers (such as Medicare and Medicaid in the United States or the Caisse Nationale d'Assurance Maladie in France), or non-governmental organizations.

In one non-limiting embodiment, the system further includes a data capture module which stores information about the injection device itself. In one embodiment, the data capture module is an electronic chip with the capability to store information about an injection such as: the type of injection device, lot and/or serial number of the device, manufacturer name, date, place of manufacture, type of medication, and the expiration date of the medication. In one embodiment, the information remains on the electronic chip even when electricity is not provided to the chip. An example of this type of electronic chip is a chip having erasable programmable read-only memory (EEPROM). In this embodiment, data is stored as blocks which can be individually written to and erased. It is further understood that, in this configuration, data contained on the chip can be deleted, added to, and read over and over again throughout the lifecycle of the chip. In some embodiments of the electronic chip, data can be written to or read from the chip without requiring physical contact to the chip. For example, the contents of the chip could be modified through magnetic induction. In certain configurations, the electronic chip could be positioned either on the surface of the injection system or embedded in a component of the injection system, such as a needle shield, a rigid needle shield, and/or a plastic rigid tip cap.

The patient or user can review the data collected by the needle 12 using a Smartphone A running a software application that functions as a dedicated user interface. The information can also be sent directly to selected stakeholders or to remote data servers using the Smartphone's communications equipment. In one embodiment, the Smartphone A also hosts software for controlling the injection device 10. For example, the user may be required to press an electronic button on the Smartphone A screen to begin the injection. The user interface software may alert the user when the injection is complete by presenting an indication on the Smartphone A screen. In certain embodiments, it should also be appreciated that, for patient adherence monitoring purposes, the prescription and medication intake schedule may be stored in the Smartphone A.

Figure 1B:
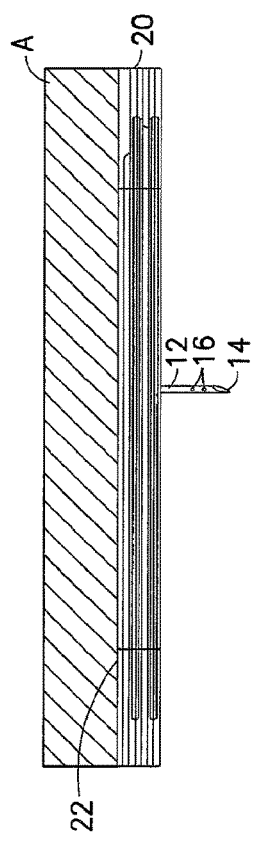
FIG. 1B is a side view of the injection device and Smartphone of FIG. 1A in accordance with an embodiment of the present invention.
Figure 2:
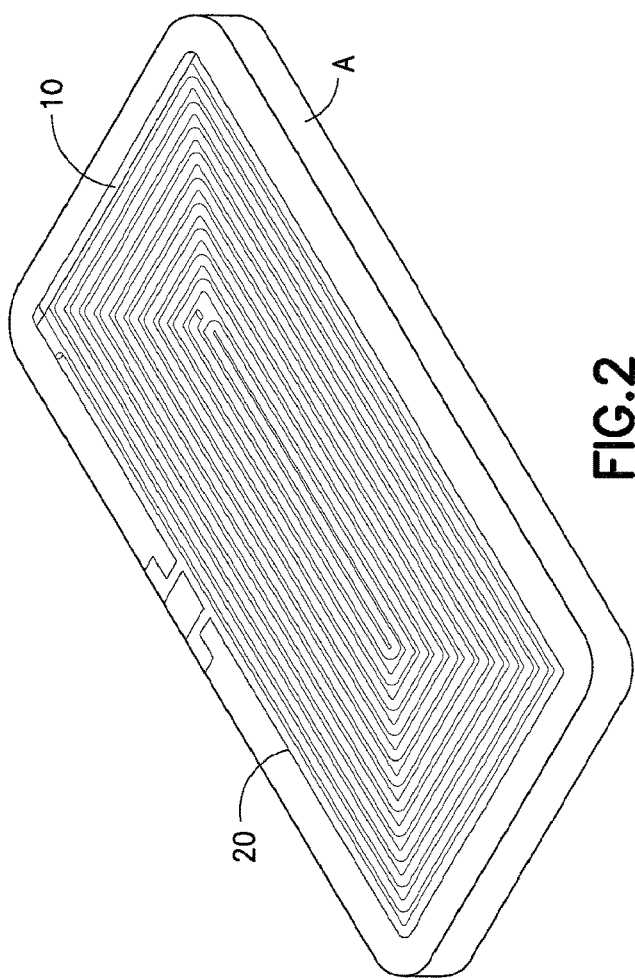
FIG. 2 is a perspective view of a bottom portion of the injection device and Smartphone of FIG. 1A in accordance with an embodiment of the present invention.

With reference now to FIGS. 1A-2, the injection device 10 further includes an external housing portion 20. The needle 12 extends through the external housing portion 20. In one embodiment, a top portion 22 of the external housing 20 is adapted to adhere to a bottom face of a handheld electronic communications device such as the Smartphone A. An electrical connection may be established between the injection device and Smartphone A using any commercially available data connection assembly such as a Universal Serial Bus (USB) port or a Firewire port. Both electricity to power the injection device and data from sensors included on the needle may be transferred between the Smartphone A and injection device 10 through the wired connection. Alternatively, the connection between the injection device 10 and Smartphone A may be a wireless connection. A battery of the injection device may be recharged through wireless magnetic induction. Data may be transferred between the devices using any commercially available wireless protocol such as WiFi. WiFi is a wireless data transmission protocol using radio waves to transmit digital data based on the IEEE 802.11 standard. Additional exemplary commercially available wireless communications modules include wireless antennas that transmit Bluetooth, Near Field Communication (NFC), Zigbee, or ANT signals. Generally, Bluetooth is preferable for low power applications where data only needs to be transmitted a short distance. WiFi has greater power consumption, but also has a greater data transmission range. In use, the injection device 10 is adapted to be placed flat on the skin of a patient, so that the needle 12 pierces the skin establishing fluid access to subcutaneous tissue. The user actuates the injection device 10, according to one of the actuation mechanisms described in greater detail below, causing a pharmaceutical agent contained therein to be expelled from the injection device 10, through a cannula (not shown) of the needle 12.

Figure 3A:
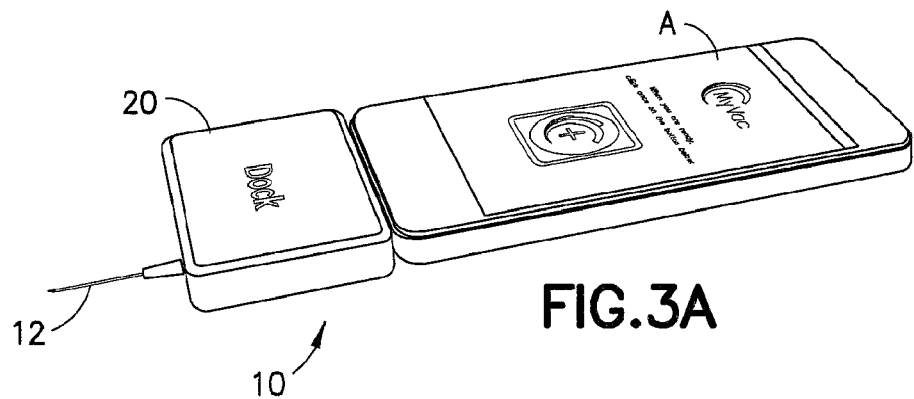
FIG. 3A is a perspective view of an injection device connected to a Smartphone in accordance with an embodiment of the present invention.
Figure 3B:
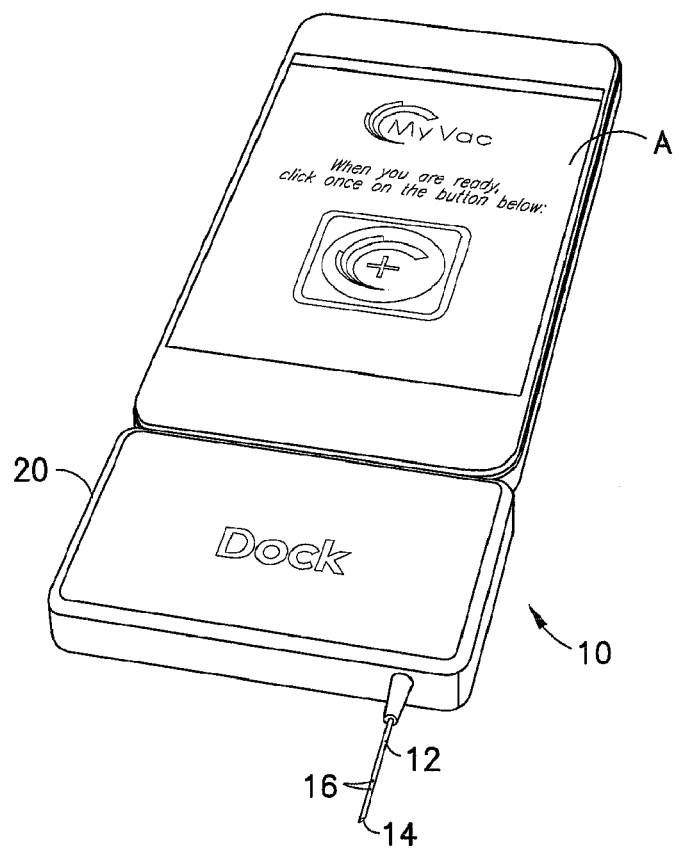
FIG. 3B is a perspective view of the injection device of FIG. 3A in accordance with an embodiment of the present invention.
Figure 4:
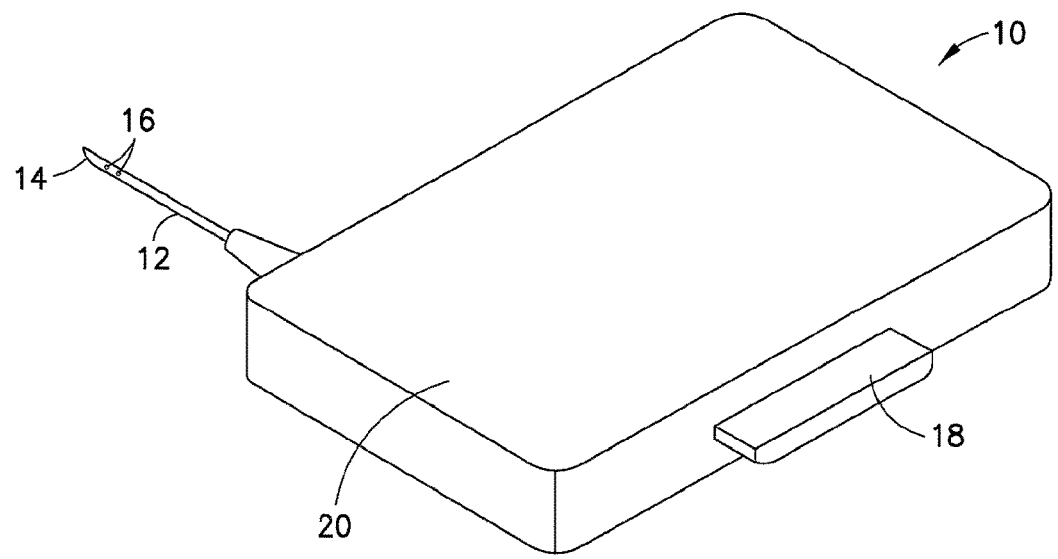
FIG. 4 is a perspective view of the injection device of FIG. 3A in accordance with an embodiment of the present invention.
Figure 5A:
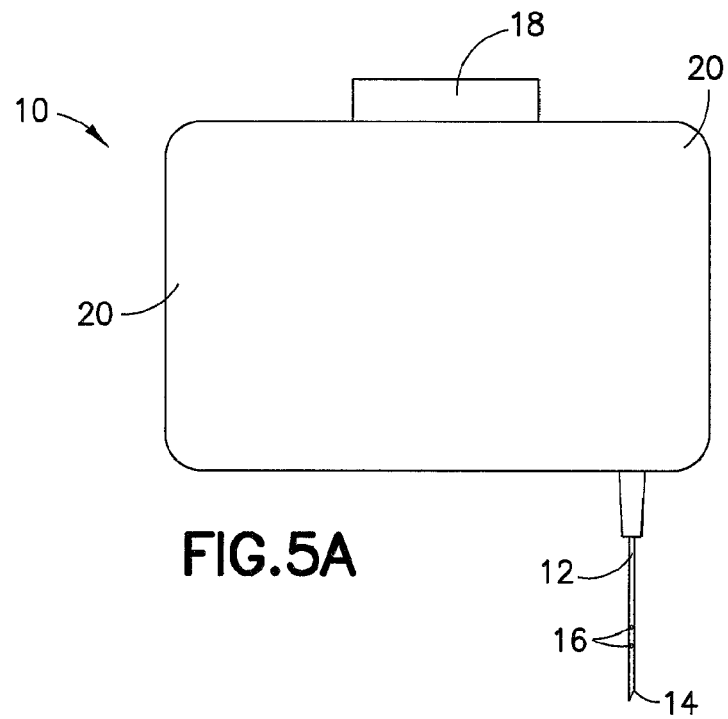
FIG. 5A is a top view of the injection device of FIG. 3A in accordance with an embodiment of the present invention.
Figure 5B:
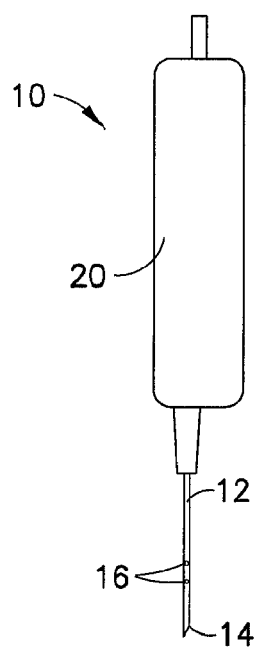
FIG. 5B is a side view of the injection device of FIG. 3A in accordance with an embodiment of the present invention.

With reference to FIGS. 3A-4, a further non-limiting embodiment of the injection device is depicted in connection with the Smartphone A. The injection device includes a pin connector 18 extending from a side of the injection device 10 adapted for insertion into a corresponding port of the Smartphone A. The pin connector 18 is used to transfer data and instructions between the injection device 10 and the Smartphone A. In certain configurations, the pin connector 18 is a pinout adapted to be received by a Universal Serial Bus (USB) port. To conserve space and to ensure that the injection device 10 is compatible with numerous commercially available cell phones, the pinout could be configured as a mini-USB or micro-USB plug.

The Smartphone A may provide power directly to the electronic chip and other elements of the injection device 10. Alternatively, the electronic chip may include an embedded power supply such as a thin film battery. In a further embodiment, the electronic chip has an embedded chargeable battery which can be wirelessly charged through an external device by means of electromagnetic induction. Alternatively, the electronic chip is powered with energy provided by an energy-harvesting device, which is also fitted on the injection device 10. In an exemplary embodiment, the energy-harvesting device is a motion generator powered from a moving part of the injection device 10. Alternatively, body heat may be used to generate electricity to power the electronic chip.

In a further embodiment, the electronic chip is a passive RFID tag equipped with non-volatile memory which is affixed to a portion of the injection device 10. Advantageously, a passive RFID tag does not need to receive power for operation. The RFID tag is read using an externally powered reading device. A further advantage of RFID technology is that the RFID tag can be read without requiring physical contact between the tag and the external reader. Instead, information contained on the chip or RFID tag is transmitted to the reader through magnetic induction. It is further understood that the reading device may include a wireless communication transmitter such as a Bluetooth, WiFi, NFC (near field communication), Zigbee, or ANT antenna. The wireless transmitter allows data uploaded from the injection device 10 to the reader to be transmitted to other external devices for storage, collection, and analysis. For example, the data may be transferred to a handheld electronic device such as a Smartphone, tablet, or laptop computer. The user or patient may use these electronic devices to review the collected data. The system may further include interface software which categorizes and presents the recorded data in a form which is easily understood by users. As with other embodiments of the integrated system described above, the data can also be sent directly from the reader to selected stakeholders or to remote data servers for further exploitation by interested third parties such as family members, doctors, care givers, or disease management companies.

In use, an integrated injection system according to any of the above described configurations could be used for inventory management, tracing specific medications from production to injection, and to prevent counterfeiting of the injection device or pharmaceutical agent. For example, reading devices can be placed at key locations along the distribution chain such as the injection device manufacturer, the pharmaceutical company's filling plants, distributor warehouses, retailers, and the location of the actual user. Throughout the distribution chain, authorized personnel may "write" additional information about the manufacturing and distribution process to the electronic chip using a dedicated data-entry device with appropriate security features. The information can be read at later points during the distribution chain and/or manufacturing either by a dedicated device or by a general purpose handheld device such as a Smartphone.

Generally, any entity within the production and distribution chain would be permitted to read data contained on the electronic chip or RFID tag. To prevent counterfeiting and other security breaches, writing capabilities should be restricted only to authorized personnel using dedicated devices developed for that purpose. In one embodiment, "reading" may also include sending the reader's information (location, identification, date, time) to a selected party through any secured wireless or wired data communication protocol. For example, the originator (e.g., the manufacturer) may ship the device to a distributor. When the device is "read" by a reader located at the distribution facility, a message is sent to the originator alerting it that the product has been received. In this way, the system can be used to help monitor shipping lead times, thereby optimizing the distribution network.

Using the same system, one can quickly and easily locate an entire batch of products in case of a product recall, thereby speeding up recall operations. Most advantageously, the system enables a user to gather real time data on manufacturing and distribution performance.

In an alternative embodiment, the system of the present invention may be used to improve adherence and monitoring of medication distribution and administration such as, for example, for chronic disease management. Specifically, a system according to the present invention can be used to record and transmit data concerning the usage of the device, including whether or not the pharmaceutical agent was successfully injected into the body of a patient. In one embodiment, this usage information is collected by passing the injection device in close proximity to a reader after injection occurs. For example, in the case of a disposable device, the reader could be situated at the opening of the disposal container to record that the empty device was appropriately disposed. For non-disposable devices, activation of the device can trigger the transmission of data that injection has occurred to concerned parties.

In some cases, merely recording that the pharmaceutical agent was expelled from the device may not be sufficient to satisfy concerned parties. Instead, proof that the agent was injected to the patient's body may be required. In that case, in one embodiment of the present invention, an electrical signal with a predefined waveform is sent from the electronic chip through the injection needle into the body of the patient. As a result of the conductivity of the body, this predefined signal can be identified and processed by a receiver placed on another area of the patient's body. If the waveform of the signal measured by the receiver is substantially similar to the reference injection signal waveform, it is assumed that the injection was completed. Upon indication of a completed injection, data related to the injection time, location, as well as other data, is transmitted to interested parties using the data transmission capabilities of the injection device itself or the attached electronic device.

By collecting this data regarding the injection, the duration and frequency of the injection can be compared to the prescribed dose to evaluate the patient's overall adherence level. For adherence monitoring purposes, the prescription and medication intake schedule may be stored in either the reading device memory or in the user's Smartphone memory. In addition, application software contained in the dedicated reader or on the attached Smartphone or tablet can be designed to send reminders to the patient before each scheduled injection. More urgent reminders can be sent to the patient if a dose is missed. If the patient does not respond to the reminders in a timely fashion, additional reminders can be sent to other interested parties such as a family member, caregiver, the medical professional that prescribed the medication, or a specialized adherence coaching service that can take additional steps to encourage the patient to follow the prescribed treatment regime.

In one embodiment, the system can be adopted for use by a disease management company (DMC). The DMC can use data recorded from the device to personalize efforts toward members who are least willing to adhere to medical instructions. Therefore, DMCs are better able to target resources to those members most in need of additional care or supervision. For example, according to one embodiment of the system, DMCs and health insurance companies would enroll their members in programs in which use of such integral injection devices is mandatory. Members could be offered incentives such as better coverage or reduced rates as long as the patient maintains a required adherence level.

In addition to monitoring patient adherence, information about patient adherence could be sent to a pharmacy to improve inventory management. The information could also be used by the pharmacy to automatically refill a patient's prescriptions at the appropriate time, further reducing the amount of responsibility for taking medication required of the patient.

With continued reference to FIGS. 1A-5B, various injection devices 10 for use with the integrated drug delivery system are depicted. In one embodiment, the relationship between the size of an external housing 20 of the injection device 10 and an internal reservoir 30, as shown in FIGS. 6B-8A, which contains the pharmaceutical agent is optimized to improve "human factors" such as factors which increase the user's confidence in performing an injection using the device. Human factors may also include: the ease of using the device for individuals without medical training; a user's perception that the injection will be error-free; confidence at the end of the dose that the entire dose was administered; and confidence that the user will not miss scheduled times to administer the medication. Generally, it is understood that the device should have a more "intelligent" design that requires less medical training and a simpler administration protocol so that non-healthcare professionals are able perform the injection without requiring the help of a trained medical professional.

The present invention further recognizes that compacity ratio is an effective indication of the relationship between the drug delivery portion of the device and other portions of the device designed to improve the user experience. Compacity ratio is defined as:

$$\text{Compacity ratio} = V°/V$$

In the above equation, $V°$ is the total volume of the injection device including an actuator, reservoir, connection, or plunger. $V$ is the volume of liquid to be delivered to the patient. Compacity ratio gives an indication of the optimization of space inside a Microelectromechanical System (MEMS) device and indicates how much of the volume of the MEMS is close to the volume of liquid available for delivery. The higher the compacity ratio, the greater the likelihood that the device was designed based on human characteristics and considerations rather than functional considerations related to the size of the drug delivery portion of the device.

With reference now to FIGS. 6A-8B, a drug delivery portion 28 of the injection device 10, according to one non-limiting embodiment of the invention, is depicted. The drug delivery portion 28 includes a delivery structure such as a needle 12 in fluid communication with an internal reservoir 30 including a fluid. Alternative structures for facilitating fluid delivery include a catheter for injections, a straw for oral delivery, or a nozzle for nasal or pulmonary delivery. In the embodiment of FIGS. 8A and 8B, the needle 12 is a hollow miniaturized needle with a patient puncture tip 24 on one end of the device and an opposite end 26 in connection with the fluid containing reservoir 30. A cannula (not shown) extends longitudinally through the needle forming a passageway for fluid flow. The needle 12 can be formed from any material having suitable strength properties and which can be sharpened to a tip sufficient to pierce the skin of a user. Exemplary materials include metals, metal alloys, and medical grade high density polymers. While the dimensions of the needle 12 are largely dependent on the type of therapeutic agent or drug for which the apparatus is being prepared, for intradermal vaccination purposes, the needle 12 will be about 2 to 4 mm in length with a cross-sectional diameter of about 0.3 to 0.5 mm. In use, according to one embodiment of the present invention, the needle 12 extends from the base of the drug delivery portion 28 of the injection device 10 by about 1 to 2 mm, allowing the needle 12 to enter the skin of a user to a depth of between 1 and 2 mm.

It is further understood that the needle 12 may be adapted to further reduce the pain of injection, thereby reducing the fear and anticipation often associated with having an injection performed. As stated above, fear and anticipation are two of the "human factors" which discourage potential users from adopting self-injection devices and techniques. Generally, pain from an injection results from the pH or ionic force of the injected solution, as well as the tearing apart of internal tissues to "free" a space within the internal tissues capable of receiving the volume of liquid injected, rather than from the injury to the skin. Therefore, pain relief methods may be used to counteract these solution forces to effectively reduce pain. For example, an anesthetic or pain reliever or analgesics could be coated on the needle 12. The pain reliever could be in the form of a hydrophobic polymer coating on the surface of the needle 12 which diffuses to the patient's skin following injection to relieve the pain sensation. In one embodiment, the analgesics or anesthetic, such as lidocaine, prilocaine, tetracaine, ametop gel, or tramadol, is dissolved or dispersed or emulsified in silicone oil, and the mixture is spray or dip-coated on the needle. Alternatively, salts embedded on the needle surface have a similar pain reducing effect by counteracting the ionic force of the injected solution. Analgesics or other topical numbing agents, such as lidocaine, prilocaine, tetracaine, ametop gel, or tramadol, may also be applied to the patient's skin prior to performing the injection and/or vaccination to reduce the pain sensation associated with skin penetration by the needle. In a further embodiment, the needle and zone of contact with the skin may be impregnated with a numbing agent, e.g., ethyl chloride, which numbs the skin around the injection site as the material evaporates.

The delivery structure or needle 12 establishes fluid communication between the reservoir 30 and the patient. The reservoir 30 is emptied by an expulsion mechanism. According to one non-limiting embodiment of the device, the reservoir 30 plays an active part in expulsion of fluid. For example, a plunger-type part may push the liquid through the reservoir for expulsion from the needle. Alternatively, a part of the reservoir 30 may be deformable and can be pressed to expel the liquid (e.g., a collapsible reservoir as in a microinfuser). According to other embodiments of the present invention, the reservoir 30 is passive and does not contain or embody structure for expelling fluid. Instead, the reservoir merely contains the liquid, and an external pumping mechanism draws the liquid out of the reservoir.

In most areas of the body, an injection of 1 to 2 mm in depth pierces and extends through the epidermis layer of skin allowing for delivery of drug directly to the dermis. Advantageously, many therapeutic agents that cannot diffuse through the epidermis are able to diffuse through the dermis layer. It is noted, however, that the depth of the epidermis varies and is, in some areas of skin, as thick as 1.5 mm. For injection intended to be delivered in locations where skin is thicker, the puncture depth must be increased to compensate for increased skin thickness.

Figure 6A:
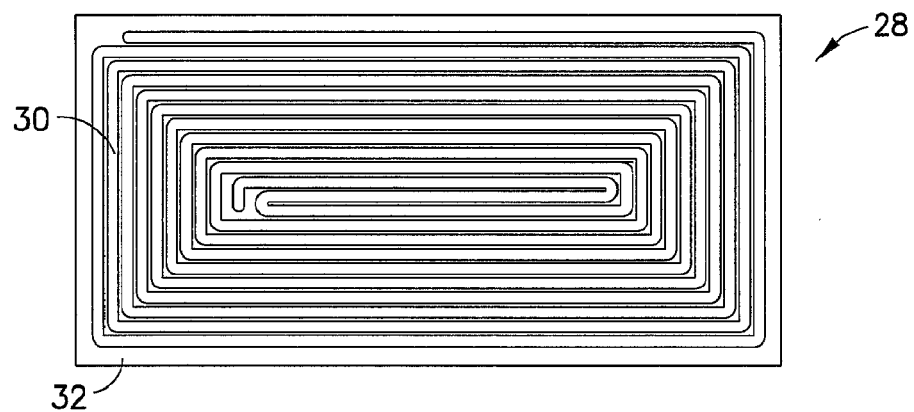
FIG. 6A is a top view of a fluid reservoir of an injection device in accordance with an embodiment of the present invention.
Figure 6B:
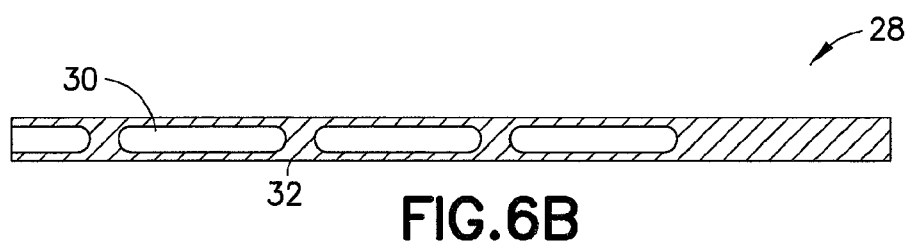
FIG. 6B is a side view of the fluid reservoir of FIG. 6A in accordance with an embodiment of the present invention.
Figure 7A:
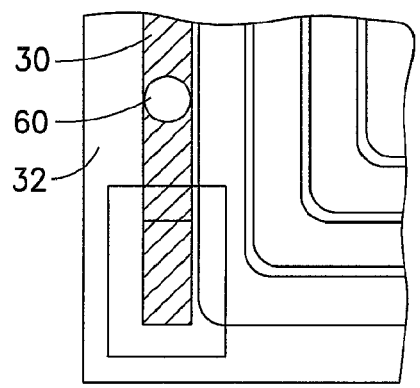
FIG. 7A is an enlarged partial top view of the fluid reservoir of FIG. 6A in accordance with an embodiment of the present invention.
Figure 7B:
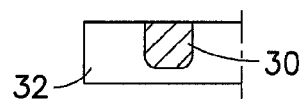
FIG. 7B is an enlarged partial side view of the fluid reservoir of FIG. 6A in accordance with an embodiment of the present invention.

With reference to FIGS. 6A and 6B, the reservoir 30 containing a therapeutic agent is formed within a substrate layer 32 of the delivery portion 28 of the device. According to one non-limiting embodiment, the reservoir is a circular labyrinth formed on a surface of the substrate layer 32. The substrate is made from silicon or glass, and more generally from any material which can be patterned by lithography and etched to form a reservoir 30. The choice of material for the substrate layer 32 is driven largely by the composition of the therapeutic agent contained in the reservoir 30. Specifically, the substrate material should be non-reactive with the therapeutic agent. Glass, for example borosilicate type 1 glass, is largely inert and non-reactive making it an excellent substrate material for many applications. Glass is also impenetrable to both water and oxygen. Alternatively, the reservoir may be a pre-manufactured structure which is affixed to the substrate layer 32. The needle 12 extends from the reservoir 30 through the substrate layer 32. The volume of the reservoir 30 is chosen to correspond closely to the volume of a single dose of the therapeutic agent to be delivered to the user. By configuring the reservoir 30 based on dose volume, the fluid to be injected takes up a majority of the reservoir volume leaving very little wasted space and reducing the overall size of the delivery portion 28 of the device. In contrast, with traditional syringes, the fluid may only fill a third or less of the total reservoir volume.

The compacity ratio described above provides an indication of the relationship between the volume of fluid to be injected and the total volume of the device. While the present invention seeks to avoid wasted space within the reservoir itself, it is noted that the fluid volume should, nevertheless, be small compared with the total volume of the injection portion of the device. In that way, human factors, rather than the configuration of the reservoir itself, can guide the design of the device.

With reference to FIGS. 6A-8B, the drug delivery portion 28 further includes an activator (not shown) and a fluid expulsion mechanism 50. The activator may be a raised button extending from the housing 20 of the injection device 10. Alternatively, the activator is an electrical switch which is engaged automatically when a signal is sent to the injection device 10 from the Smartphone A. The fluid is expelled from the reservoir 30 by a material which is solid at room temperature but which becomes flowable when exposed to heat. An exemplary material is paraffin wax. A heating layer 54 is deposited above the reservoir containing substrate layer 32. Specifically, the heating layer 54 contains a thin resistive film or resistance coils 56 which become hot when an electric current is passed through them. The electric current is provided by a power source such as one of the power sources described above. An expulsion reservoir 52 containing the flowable material (e.g., paraffin wax) is deposited above the heating layer 54. The expulsion reservoir 52 includes an outlet channel 58 for establishing a fluid connection between the expulsion reservoir 52 and the fluid labyrinth of the internal reservoir 30. The outlet channel 58 opens to the most distal portion (i.e., the start) of the internal reservoir 30.

When the heating layer 54 is activated, the material contained in the expulsion reservoir 52 softens and becomes flowable causing the material to flow downward through the outlet channel 58. The flowable material enters the internal reservoir 30 at its most distal portion. As the flowable material continues to enter the internal reservoir 30, it exerts force on a stopper 60 thereby forcing the stopper 60 to advance through the internal reservoir 30. The stopper 60 can be a wide variety of structures or materials which maintain separation between the flowable material and fluid therapeutic agent. Notably, the material should not degrade in response to heat or adversely interact with either the fluid contained in the reservoir or the flowable material. In one non-limiting embodiment, the stopper 60 is a small amount of silicone oil. As the stopper 60 advances through the reservoir 30, fluid contained therein is forced toward the center of the reservoir 30. The fluid exits the reservoir through the needle 12 located in the reservoir 30 center for delivery to the user.

Figure 9:
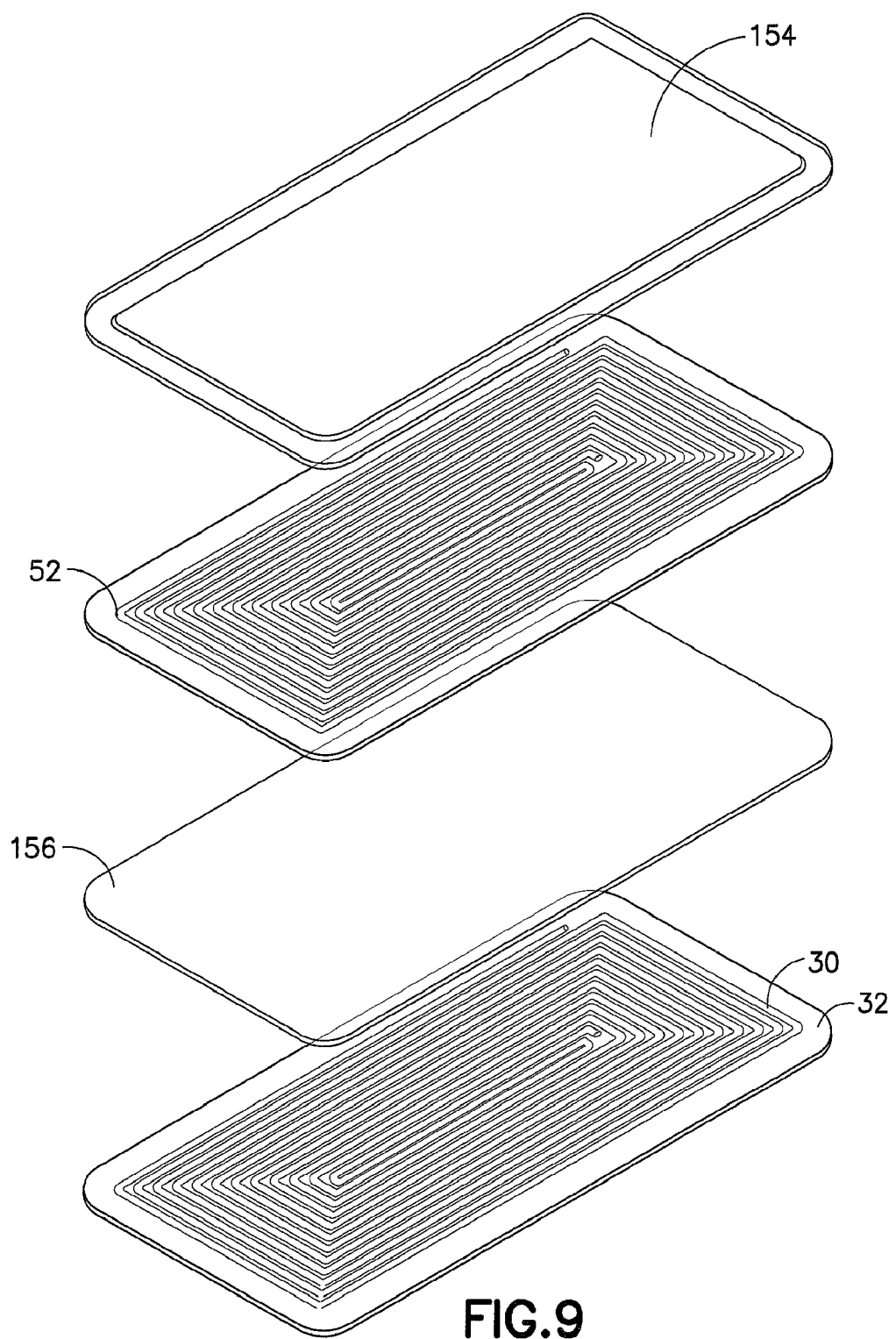
FIG. 9 is an exploded perspective view of a drug delivery portion of an injection device in accordance with an embodiment of the present invention.

With reference now to FIG. 9, according to a further non-limiting embodiment of the drug delivery portion 28 of the injection device 10, the expulsion mechanism includes an expulsion reservoir 52 comprising a labyrinth containing an actuation medium. An expandable gas layer 154 is positioned above the expulsion reservoir 52 such that the expanding gas expels fluid from the expulsion reservoir 52 by pushing down on the expulsion reservoir 52. As the gas contained in the gas layer 154 expands, the actuation fluid is driven through the labyrinth of the expulsion reservoir 52. The expulsion fluid passes from the expulsion reservoir 52 to the reservoir 30 containing the pharmaceutical agent through a port located on an outside edge of the expulsion reservoir 52. The expulsion fluid enters the fluid reservoir 30 and drives the therapeutic agent through the labyrinth of the fluid reservoir 30 causing the fluid to be expelled from the drug delivery device through the cannula of the needle. The layer containing the expulsion reservoir 52 and the layer containing the fluid reservoir 30 are separated by a permeable layer 156. The permeable gas layer 156 functions as a gas exhaust layer which is permeable to air to stop the gas actuation. Specifically, the gas from the expandable gas layer 154 can diffuse away from the drug delivery portion 28 of the device through the permeable layer 156 so that the expanded gas does not exert pressure on the reservoir layer 30 causing the therapeutic agent to be forced from the drug delivery portion 28 of the device prematurely.

Figure 10:
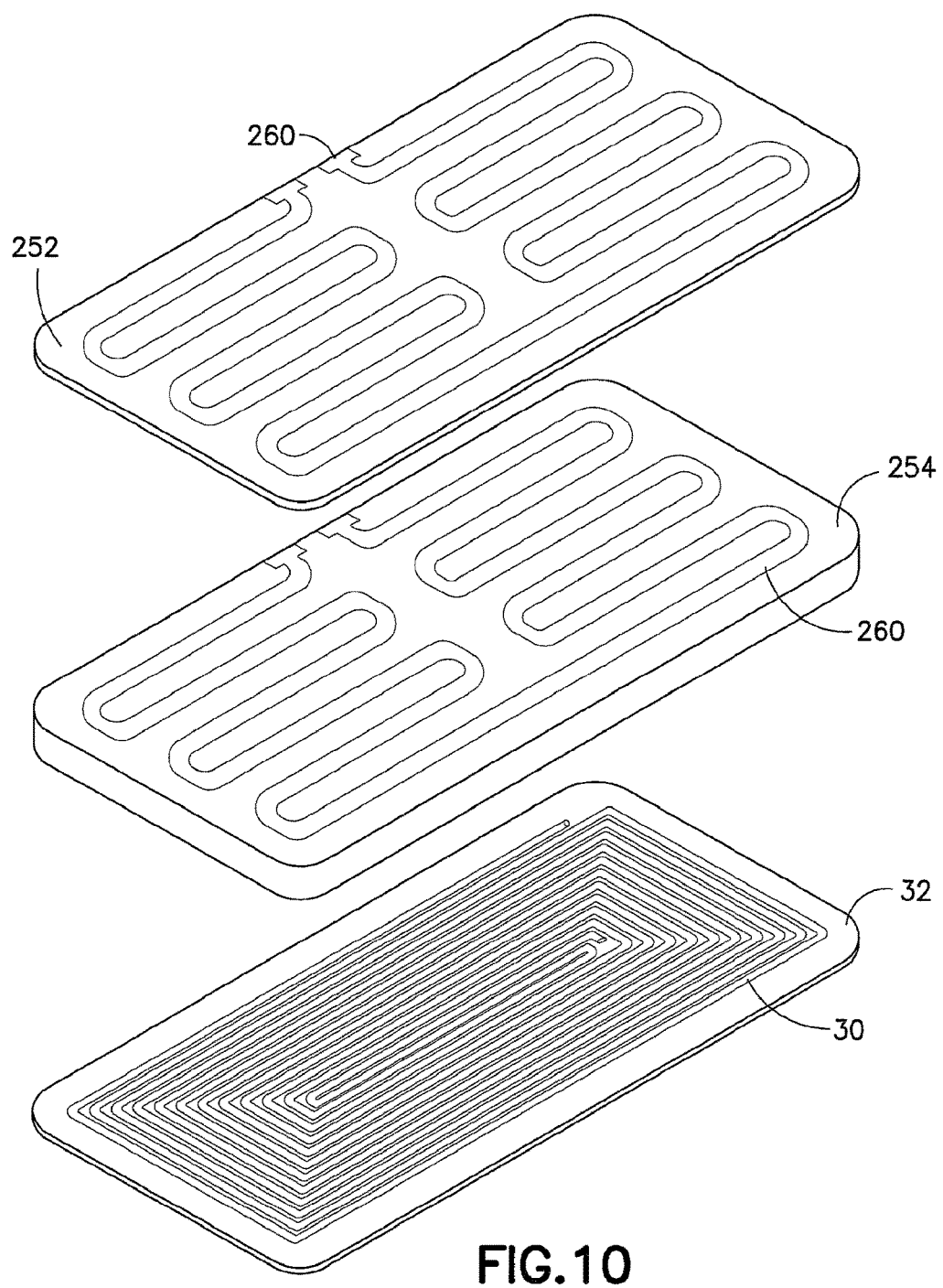
FIG. 10 is an exploded perspective view of a drug delivery portion of an injection device in accordance with an embodiment of the present invention.

With reference to FIG. 10, a further embodiment of the drug delivery portion 28 of the injection device 10 is depicted, including multiple expulsion layers 252, 254 containing the actuation material and a fluid reservoir 30 with a double labyrinth. The multiple layers each include expulsion ports 260 such that once the device is actuated, wax flows through each port 260 to the fluid reservoir 30. Wax from each expulsion layer 252, 254 flows to independent defined paths of the labyrinth through the respective expulsion ports 260. The wax from the separate expulsion layers 252, 254 advances through the separate paths of the fluid reservoir 30 simultaneously. In this way, the volume of therapeutic agent expelled from the fluid reservoir 30 of the device at one time is increased.

Figure 11:
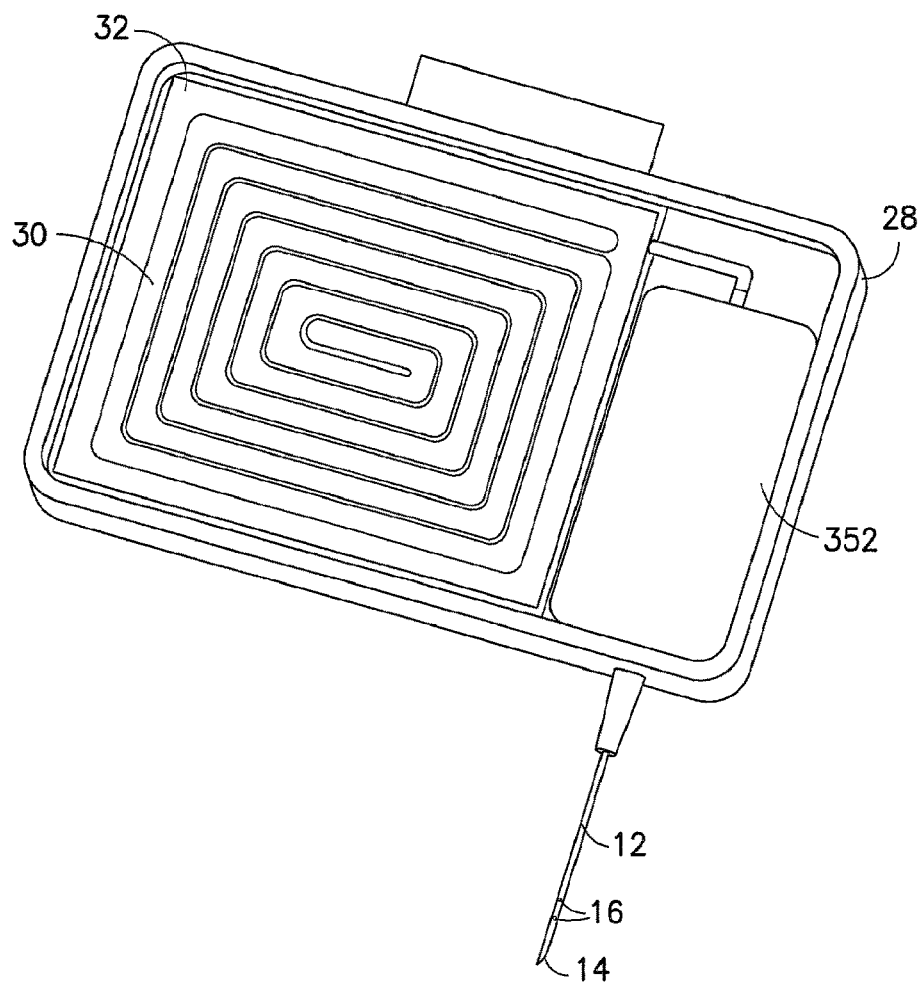
FIG. 11 is a perspective view of an injection device having a cover layer removed therefrom in accordance with an embodiment of the present invention.

With reference now to FIG. 11, according to a further non-limiting embodiment of the drug delivery portion 28, the expulsion mechanism is a piezoelectric pump 352. The pump 352 is in fluid communication with both a labyrinth shaped reservoir 30 and the cannula of a needle 12 such that, when actuated, the pump 352 draws the therapeutic agent from the reservoir 30 and expels the fluid through the needle 12. In one non-limiting embodiment, the pump 352 is a Bartels mp6 pump manufactured by Bartels Mikrotechnik GmbH of Dortmond, Germany. However, any micropump capable of being adapted to fit within the external housing may be used within the scope of the invention. The invention may also be configured to include multiple pumps to increase fluid pressure to increase the rate at which fluid is expelled from the pump.

The drug delivery portions of the self-injection device described above are designed to hold small volumes of fluid, such as a single dose of an intra-dermal injection of flu vaccine (0.1 mL) Other applications requiring small volumes of injection include intra-dermal injections of other vaccines (such as HPV), de-sensitization for allergies, and emergency pain reliever (e.g., lidocaine). However, the drug delivery device of the present invention may also be applied to larger volume injections. The above described embodiments of the drug delivery portions can be used for reservoir sizes up to about 0.5 mL. With slight modification to the design, the reservoir may be further adapted to contain a fluid volume in the range of 100 mL. One configuration capable of containing greater volumes of fluid is obtained by stacking smaller volume drug delivery chips on top of one another to create a composite chip having a greater total reservoir volume.

Figure 12A:
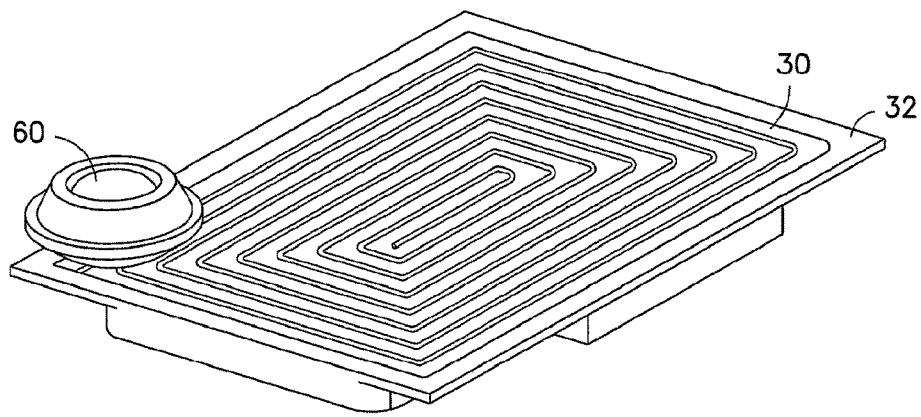
FIG. 12A is a perspective view of a drug delivery portion of an injection device in accordance with an embodiment of the present invention.
Figure 12B:
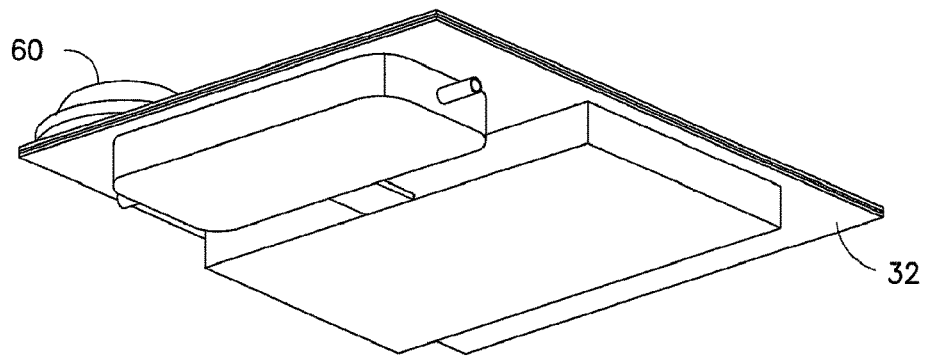
FIG. 12B is a perspective view of a bottom section of the drug delivery portion of FIG. 12A in accordance with an embodiment of the present invention.

With reference to FIGS. 12A and 12B, in one embodiment, the drug delivery device further includes a stopper 60 having a pierceable septum which can be used for filling the fluid reservoir 30. In use, a needle is inserted into the reservoir through the stopper 60. The needle may be connected to a syringe or other injection device. The user expels the fluid to the reservoir 30 through the needle using the syringe. In this way, the fluid reservoir 30 is filled and is prepared for injection to a patient.

A further aspect of the present invention is drawn to a method of manufacturing the miniaturized injection system, installing the injection system within a suitable housing, and filling the device with a therapeutic agent such as a vaccine or drug. According to one non-limiting embodiment, the manufacturing method is based largely on manufacturing processes which were developed for use in the semiconductor and electronics industry and are commonly used to make integrated circuits, electronic packages, and other microelectronic or MEMS devices. Other techniques used in the invented method of manufacture are adapted from the field of micromachining. However, the method of manufacture described below is intended only as a non-limiting exemplary method for manufacturing the injection device. It is understood that the self-injection device of the present invention can be formed in numerous other ways which do not rely on semiconductor manufacturing principles and, nevertheless, fall within the scope of the invented device and method.

It is desired that the manufacturing method permit large scale batch manufacturing of the injection device to reduce cost, as well as to permit filling of the reservoirs at a rate compatible with market needs. Batch production is a manufacturing technique in which numerous articles are prepared in parallel rather than in an assembly line fashion in which only a single device is acted on at a time. It is envisioned that batch manufacturing will increase production rate for the injection device, thereby reducing costs per device.

According to the inventive method of manufacture, a substrate is provided. Optionally, the substrate is a thin glass layer produced by any acceptable method including float processing and fusion processing (overflow down draw process). The float process (also known as the Pilkington process) involves floating molten glass on a bed of molten metal to create a sheet of uniform thickness. In the fusion production method, molten glass is permitted to flow down opposite sides of a tapered trough forming two thin molten streams. The two glass streams rejoin or fuse at the base of the trough forming a single sheet having excellent uniformity of depth and composition. The fusion process is a technique for producing flat glass often used in the manufacture of flat panel displays. Advantageously, the technique produces glass with a more pristine surface, as the surface is not touched by molten metal. Glass produced by this technique is widely commercially available and is produced by companies including Schott, Corning, Samsung, and Nippon Electronic Glass. Alternatively, substrate materials including medical grade polymers and silicon could also be used within the scope of the invented method.

The substrate is provided as a large sheet on which numerous drug delivery devices will be formed. Recent advances in glass fabrication techniques (especially in the field of flat glass for flat panel displays) have greatly increased the size of flat glass panels which are commercially available. Currently, panels encompassing several square meters are commercially available. In one preferred embodiment of the present method, 8×8- to 17×17-inch square glass wafers, which can be manufactured to contain between about 40 and 200 delivery devices, are used as a substrate material.

Once the substrate is provided, the reservoirs or cavities are formed on the substrate. A person of skill in the art will recognize that many techniques exist for forming a depression in a glass substrate which will serve as a fluid containing cavity. According to one embodiment, the cavity is formed by wet etching in which a strong acid (e.g., hydrofluoric acid) is exposed to unprotected portions of the glass surface. The depth of the etched cavity can be approximately controlled by estimating the decomposition rate of the substrate based on the composition of the reagent. It is understood that some reagents are isotropic in that they cause the substrate to degrade at an equal rate in all directions forming a hemispherical depression. Anisotropic reagents only degrade the substrate in the vertical (depth) direction resulting in depressions that are essentially rectangular in shape. It is understood that other etching techniques may also be used to form the reservoir including plasma (dry) etching, in which a high-speed stream of plasma (e.g., glow discharge particles) on an appropriate gas mixture is shot at the sample to form the depression. It is also possible to attach a pre-formed reservoir to the substrate rather than forming the reservoir within the substrate. As described above, the dimensions of the cavity or reservoir should be as small as possible, but sufficient to hold a single dose of drug or vaccine. According to one embodiment of the invention, adopted for use with flu vaccine, the reservoir is 100 μL.

Once the reservoir is formed, the microneedle is placed in the reservoir. As described above, the microneedle is a hollow needle formed from metal or other suitably strong material. The needle is placed using an automated "pick and place" machine similar to machines used for placing transistors on a circuit board. It is further envisioned, according to one embodiment of the method, that multiple needles will be placed in separate reservoirs of the wafer at the same time. In this way, the time required to produce each delivery device and reservoir on the substrate can be significantly reduced. Optionally, the microneedle is anchored to the substrate using an adhesive material such as glue. In addition, the microneedle structure may further include a stopper material to prevent the fluid from being expelled from the reservoir prematurely. For example, a thin breakable film or membrane may be included within the needle lumen. The film or membrane should be sufficiently strong and stable to prevent the fluid from escaping from the reservoir. However, once the injection device is activated, and the expulsion mechanism begins to reduce the volume of the reservoir chamber, the force applied to the thin membrane is increased. In response to this increase in force, the film or membrane breaks allowing fluid to pass through the needle for delivery to the user.

Upper layers, including one or more of a thin glass membrane layer to enclose and separate the fluid reservoir from the rest of the delivery device, upper structural layers having similar dimensions and composition to the substrate layer, a drive mechanism, and an activator may be deposited above the substrate layer and fluid containing reservoir. These upper layers and mechanical structures are placed using micro-manufacturing techniques similar to the method for placing the microneedle within the reservoir. As described above, it is desirable to place components according to a batch protection method in which components for multiple injection devices are placed simultaneously.

Once the layers and components for each reservoir are assembled on the wafer substrate, the wafer is divided into individual injection devices. The wafer may be divided by any suitable process capable of making rapid exact and small cuts through the wafer. One cutting process well suited for this application is laser cutting. Mechanical and plasma cutting techniques can also be adapted for dividing the larger wafer into individual injection devices.

At some point during the manufacture or distribution process, the injection devices are filled with the vaccine or drug to be delivered to the user. One possibility is that the reservoirs can be filled during the manufacturing process before the larger wafers are separated into individual devices. In this case, the injection devices are sold to consumers as pre-filled injection devices. Alternatively, the injection devices could be filled later, such as after they are purchased by and shipped to a pharmaceutical company or pharmacy. In either case, filling can be accomplished by several approaches. The examples provided herein are but two of the multiple available methods for filling an injection device. One of skill in the art will appreciate that other filling methods are similarly available.

In one filling method, the injection device includes a second fluid channel formed in the substrate for permitting access to the reservoir. The channel is closed by an elastomeric plug. The plug is adapted to be pierced by a filling needle. The filling needle is pushed through the plug thereby providing a second source of access to the reservoir. Fluid is then pushed into the reservoir through the filling needle. Air is vented from the reservoir through the microneedle (injection needle). The filling needle is then removed from the reservoir by pulling away from the elastomeric plug. Once the filling needle is removed from the plug, the flexible elastomeric material reseals thereby preventing fluid from leaking from the reservoir Alternatively, the reservoir is filled by a vacuum suction method. According to the vacuum suction method, the injection device is placed in a vacuum chamber to evacuate air from the reservoir cavity. Once air is evacuated from the chamber, a needle from a filling machine can be injected into the reservoir and fluid injected through the needle to the reservoir. Notably, since the reservoir was evacuated by a vacuum, venting is not required since no air is contained within the reservoir. Additionally, as a result of the difference in pressure between the reservoir and the filling machine, the fluid is drawn by suction into the reservoir meaning that no pumping is required to introduce the fluid to the reservoir. Once the fluid is injected into the reservoir, the filling needle is removed and a film cap is placed over the injection site. Exemplary cap materials include a thin hydrophobic film or a UV cured polymer.

According to one embodiment of the vacuum suction filling method, the microneedle is installed after the reservoir has been filled. After filling, the microneedle is inserted into the reservoir through the film cap. The film cap then serves as a breakable septum for maintaining the fluid in the reservoir until activation occurs. Once the device is activated, the increased force against the cap or septum causes the cap to break and allows fluid to flow from the reservoir through the microneedle.

Once the injection device is fully assembled and filled, the injection portion of the device is placed in a housing. As stated above, it is necessary that the housing be visually appealing to users to encourage them to participate in optional medical procedures such as voluntary immunizations. The injection device is placed in the housing using a dedicated "pick and place" machine adapted for that purpose.

When considering the method of manufacture for the self injection device, it is understood that multiple steps which require microfabrication machines could be performed together. For example, the steps of dividing the devices by cutting the wafer and placing the individual wafers in housings could be performed simultaneously by the same "pick and place" type machine.

What is claimed is:

1. An integrated injection system, the system comprising:
an injection device comprising a drug delivery portion comprising a reservoir containing a pharmaceutical agent, the injection device further comprising a data transmitter, a data capture module including at least one sensor, and a receiver device, wherein the injection device is configured to deliver the pharmaceutical agent to a body of a patient,
wherein the data capture module is configured to sense information about a physical condition and/or a behavior of a patient during an injection event,
wherein the data transmitter is configured to be in electronic communication with a communication device that is external to the injection device, and
wherein the receiver device is configured to be placed on an area of the body of the patient during the injection event,
wherein the injection device is configured to send an electrical signal with a predefined waveform through a needle into the body of the patient, and wherein the receiver device is configured to identify and process the predefined waveform to determine if the waveform of the signal measured by the receiver device is substantially similar to a reference injection signal waveform associated with the pharmaceutical agent being successfully injected into the body of the patient to determine if the pharmaceutical agent was successfully injected into the body of the patient, and
wherein the data transmitter is configured to transmit at least a portion of the sensed information about the physical condition and/or the behavior of the patient sensed during the injection and a confirmation that the pharmaceutical agent has been successfully injected into the body of the patient to the communication device.

2. The integrated injection system of claim 1, wherein the drug delivery portion comprises a needle, and wherein the at least one sensor is located on a portion of the needle which is intended to be positioned inside the body of the patient during the injection event.

3. The integrated injection system of claim 2, wherein the at least one sensor is positioned within the body of the patient during the injection event.

4. The integrated injection system of claim 2, wherein the injection device further comprises an external housing enclosing the drug delivery portion and the data transmitter, and wherein the needle is in fluid communication with the reservoir and extendable through at least a portion of the external housing.

5. The integrated injection system of claim 4, wherein the data transmitter is configured to transmit a signal to the communication device when the pharmaceutical agent has been fully expelled from the reservoir.

6. The integrated injection system of claim 5, wherein the communication device is configured to provide an indication which alerts a user that the pharmaceutical agent has been expelled from the reservoir in response to the signal.

7. The integrated injection system of claim 1, wherein the drug delivery portion includes an activator configured to engage a drive mechanism configured to expel the pharmaceutical agent from the injection device, and wherein the activator is configured to be triggered by an activation activity performed by a user on the communication device.

8. The integrated injection system of claim 1, wherein the at least one sensor is configured to measure a physical characteristic of the patient.

9. The integrated injection system of claim 8, wherein the physical characteristic is metabolism, body temperature, heart rate, blood pressure, or body fat composition.

10. The integrated injection system of claim 1, wherein the communication device is configured to analyze at least a portion of the sensed information to determine adherence to a prescribed treatment routine.

11. The integrated injection system of claim 1, wherein the communication device is configured to analyze the sensed information in correlation with data obtained from other sources to determine adherence to a prescribed treatment routine.

12. The integrated injection system of claim 1, wherein at least one of the injection device and the communication device is configured to store the sensed information from a plurality of different injection events.

13. The integrated injection system of claim 1, wherein the injection device further comprises an electronic chip configured to store the sensed information.

14. The integrated injection system of claim 13, wherein the electronic chip is further configured to store information identifying at least one of a type of injection device, an injection time of the injection event, or an injection location of the injection event.

15. The integrated injection system of claim 14, wherein the electronic chip is configured to store additional information pertaining to a manufacturing or a distribution process of the injection device.

16. The integrated injection system of claim 1, wherein the data transmitter comprises a wireless transmitter such that the electronic communication with the communication device is performed wirelessly.

17. The integrated injection system of claim 1, wherein the data transmitter comprises a wired connection including a pin connector configured for insertion into a corresponding port of the communication device such that the electronic communication with the communication device is performed over the wired connection.

18. The integrated injection system of claim 1, wherein the injection device further comprises an internal power source.

19. The integrated injection system of claim 1, wherein the injection device is configured to receive power from the communication device.

20. The integrated injection system of claim 1, wherein the communication device is configured to transmit at least a portion of the sensed information to at least one external system.

21. The integrated injection system of claim 1, wherein the communication device comprises a user interface display configured to provide at least a portion of the sensed information to a user.

22. The integrated injection system of claim 1, wherein the communication device is a smart phone.

23. An integrated injection system, the system comprising:
an injection device comprising a drug delivery portion comprising a reservoir containing a pharmaceutical agent, the injection device further comprising a data transmitter, and a receiver device, wherein the injection device is configured to deliver the pharmaceutical agent to a body of a patient,
wherein the data transmitter is configured to be in electronic communication with a communication device that is external to the injection device, and
wherein the receiver device is configured to be placed on an area of the body of the patient during the injection event,
wherein the injection device is configured to send an electrical signal with a predefined waveform through a needle into the body of the patient, and wherein the receiver device is configured to identify and process the predefined waveform to determine if the waveform of the signal measured by the receiver device is substantially similar to a reference injection signal waveform associated with the pharmaceutical agent being successfully injected into the body of the patient to determine if the pharmaceutical agent was successfully injected into the body of the patient, and
wherein the data transmitter is configured to transmit a confirmation that the pharmaceutical agent has been successfully injected into the body of the patient to the communication device.

24. A method for monitoring an injection event, the method comprising:
delivering, by an injection device, a pharmaceutical agent to the body of a patient;
sending, by the injection device through a needle, an electrical signal with a predefined waveform into the body of the patient;
sensing, by at least one sensor of a data capture module of the injection device, information about a physical condition and/or a behavior of the patient during the injection event;
identifying and processing, with a receiver device placed on an area of the body of the patient during the injection event, the predefined waveform to determine if the waveform of the signal measured by the receiver device is substantially similar to a reference injection signal waveform associated with the pharmaceutical agent being successfully injected into the body of the patient to determine if the pharmaceutical agent was injected into the body of the patient;

establishing, by a data transmitter of the injection device, an electronic communication with a communication device that is external to the injection device; and transmitting, by the data transmitter of the injection device, at least a portion of the sensed information about the physical condition and/or the behavior of the patient sensed during the injection and a confirmation that the pharmaceutical agent has been at least partially expelled from the reservoir and successfully injected into the body of the patient to the communication device.

25. A method for monitoring an injection event, the method comprising:

delivering, by an injection device, a pharmaceutical agent to the body of a patient;

sending, by the injection device through a needle, an electrical signal with a predefined waveform into the body of the patient;

identifying and processing, with a receiver device placed on an area of the body of the patient during the injection event, the predefined waveform to determine if the waveform of the signal measured by the receiver device is substantially similar to a reference injection signal waveform associated with the pharmaceutical agent being successfully injected into the body of the patient to determine if the pharmaceutical agent was successfully injected into the body of the patient;

establishing, by a data transmitter of the injection device, an electronic communication with a communication device that is external to the injection device; and transmitting, by the data transmitter of the injection device, a confirmation that the pharmaceutical agent has been at least partially expelled from the reservoir and successfully injected into the body of the patient to the communication device.

* * * * *